(12) United States Patent
Shibata et al.

(10) Patent No.: US 10,709,421 B2
(45) Date of Patent: Jul. 14, 2020

(54) ULTRASOUND DIAGNOSTIC APPARATUS

(71) Applicant: Toshiba Medical Systems Corporation, Otawara-shi (JP)

(72) Inventors: Chihiro Shibata, Nasushiobara (JP); Akihiro Kakee, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 580 days.

(21) Appl. No.: 15/417,771

(22) Filed: Jan. 27, 2017

(65) Prior Publication Data

US 2017/0224307 A1  Aug. 10, 2017

(30) Foreign Application Priority Data

Feb. 10, 2016 (JP) .................................. 2016-024096
Nov. 10, 2016 (JP) .................................. 2016-219857

(51) Int. Cl.
*A61B 8/00* (2006.01)
*A61B 8/06* (2006.01)
*A61B 8/08* (2006.01)

(52) U.S. Cl.
CPC ................ *A61B 8/463* (2013.01); *A61B 8/06* (2013.01); *A61B 8/4494* (2013.01); *A61B 8/488* (2013.01); *A61B 8/5246* (2013.01)

(58) Field of Classification Search
None
See application file for complete search history.

(56) References Cited

U.S. PATENT DOCUMENTS

| 5,279,302 | A | * | 1/1994 | Tamano | ............ G01S 15/8979 600/455 |
| 5,910,117 | A | * | 6/1999 | Basoglu | ................ A61B 8/488 600/454 |
| 7,503,896 | B2 | * | 3/2009 | Miele | ................ A61B 5/02028 600/301 |

(Continued)

FOREIGN PATENT DOCUMENTS

| JP | 2008-92981 | 4/2008 |
| JP | 2014-42823 | 3/2014 |
| JP | 2014-158698 | 9/2014 |

*Primary Examiner* — Carl H Layno
*Assistant Examiner* — Manolis Pahakis
(74) *Attorney, Agent, or Firm* — Oblon, McClelland, Maier & Neustadt, L.L.P.

(57) ABSTRACT

An ultrasound diagnostic apparatus according to an embodiment includes processing circuitry. The processing circuitry causes an ultrasound probe to execute first ultrasound scanning to acquire blood flow information within a first scanning area and causes the ultrasound probe to execute second ultrasound scanning to acquire tissue shape information within a second scanning area. The processing circuitry receives an instruction for changing a flow-velocity value to be displayed in display of the blood flow information. When, because of a change of the flow-velocity value according to the instruction, a time for transmitting/receiving ultrasound per scanning line in the first ultrasound scanning exceeds a transmitting/receiving time before the change, the processing circuitry assigns a time corresponding to the excess to at least one of the first ultrasound scanning and the second ultrasound scanning.

5 Claims, 9 Drawing Sheets

(56) References Cited

U.S. PATENT DOCUMENTS

| | | | |
|---|---|---|---|
| 2009/0012398 A1* | 1/2009 | Zhang | G01S 7/52077 600/453 |
| 2012/0123271 A1* | 5/2012 | Cai | A61B 8/06 600/454 |
| 2012/0152021 A1* | 6/2012 | Ma | A61B 8/06 73/632 |
| 2013/0090560 A1* | 4/2013 | Kotaki | A61B 8/14 600/443 |
| 2013/0281855 A1* | 10/2013 | Baba | A61B 8/06 600/441 |
| 2013/0345564 A1* | 12/2013 | Nakaya | A61B 8/5246 600/441 |
| 2014/0039317 A1* | 2/2014 | Sato | A61B 8/54 600/443 |
| 2015/0141821 A1* | 5/2015 | Yoshikawa | A61B 8/5207 600/438 |
| 2015/0320395 A1 | 11/2015 | Sato | |
| 2016/0151039 A1* | 6/2016 | Morikawa | A61B 8/0841 600/424 |
| 2017/0071567 A1* | 3/2017 | Shibata | A61B 8/06 |
| 2017/0224309 A1* | 8/2017 | Imamura | A61B 8/488 |

* cited by examiner

FIG.3
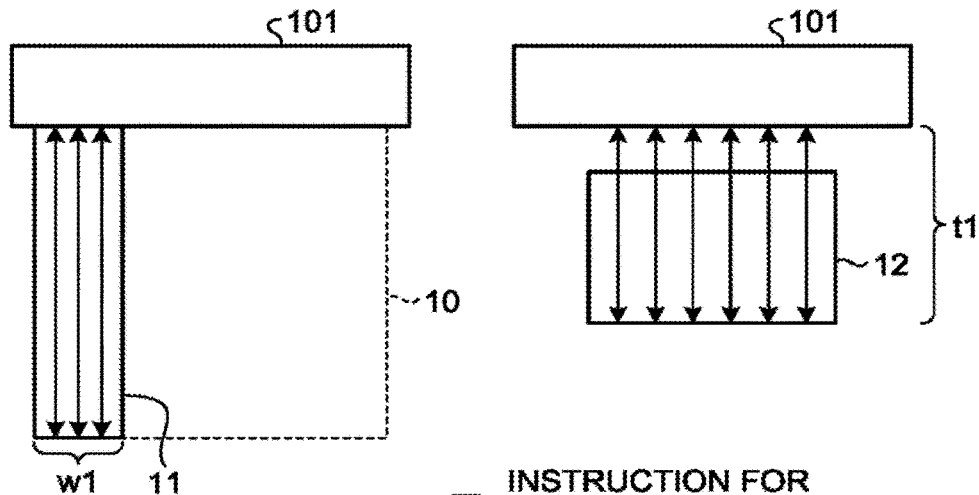
⇩ INSTRUCTION FOR LOWERING UPPER LIMIT OF FLOW-VELOCITY RANGE
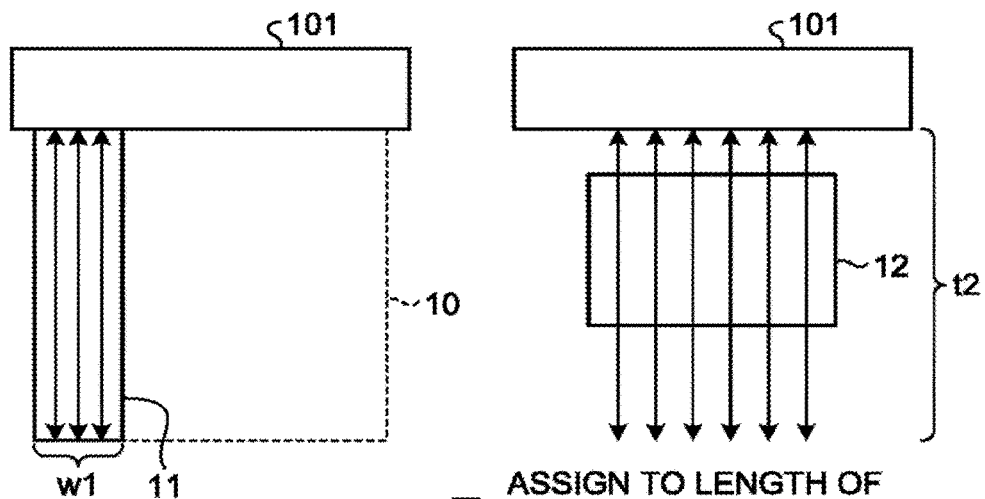
⇩ ASSIGN TO LENGTH OF DIVIDED AREA IN ORIENTATION DIRECTION
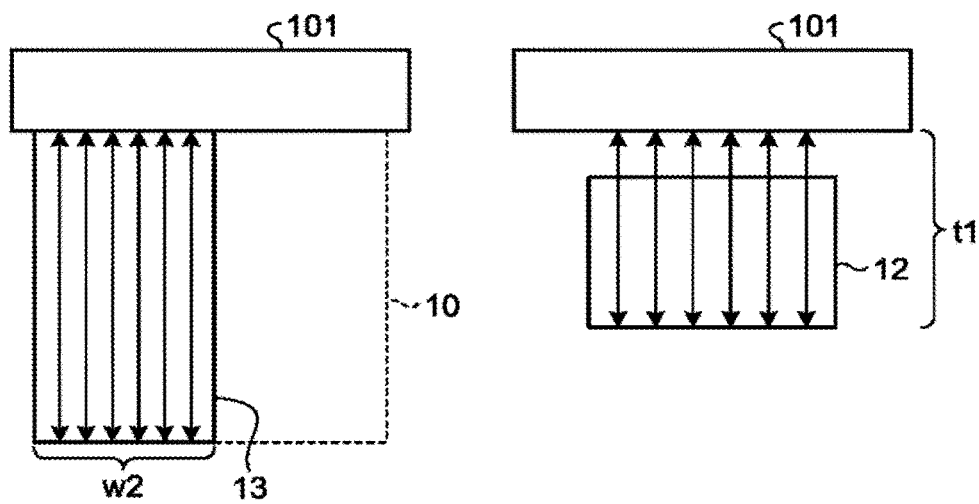

ASSIGNMENT TO DENSITY OF SCANNING LINES IN BLOOD-FLOW IMAGE

FIG.8
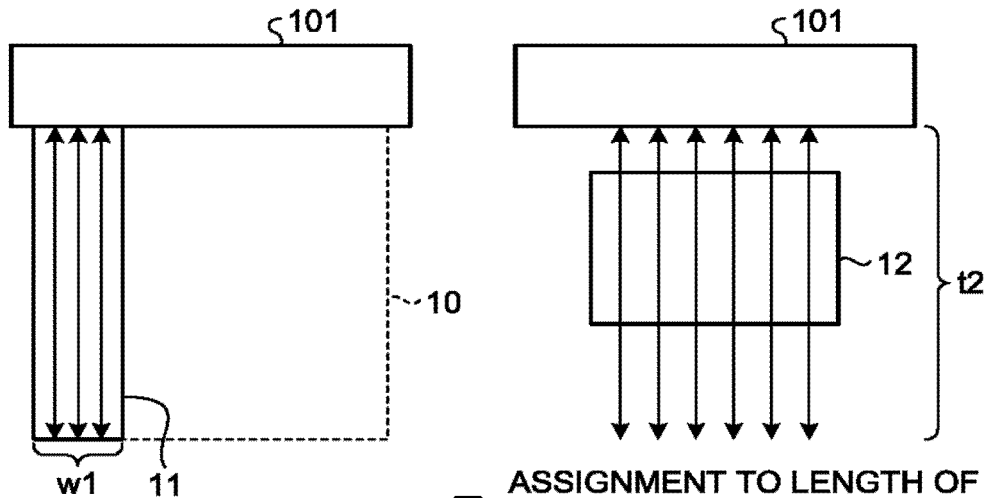
ASSIGNMENT TO LENGTH OF DIVIDED AREA IN ORIENTATION DIRECTION AND DENSITY OF SCANNING LINES IN BLOOD-FLOW IMAGE
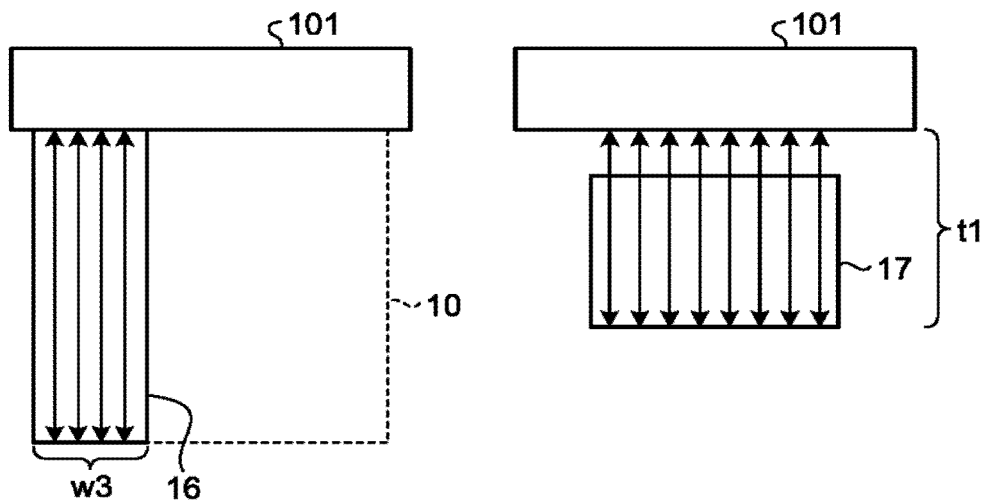

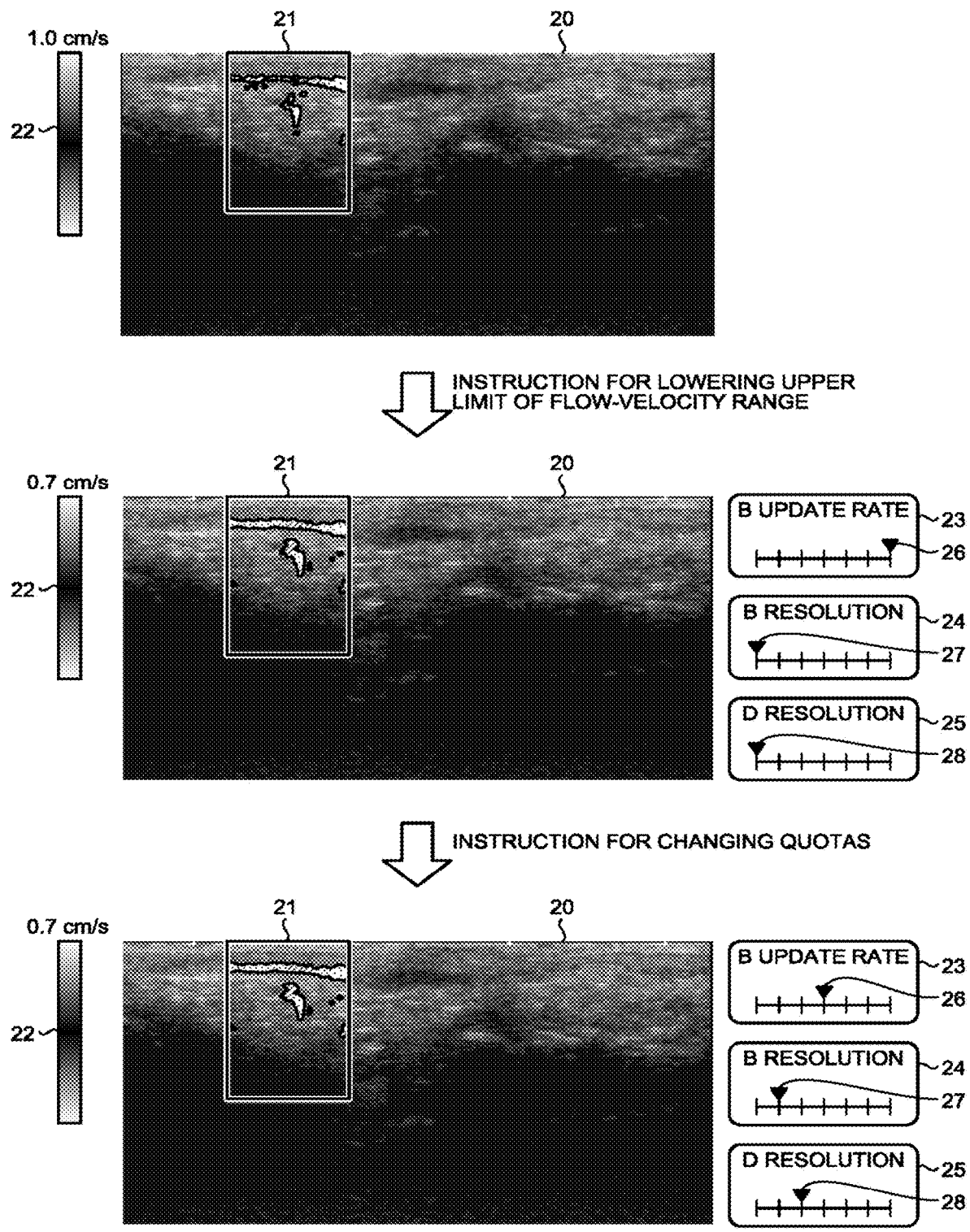

ULTRASOUND DIAGNOSTIC APPARATUS

CROSS-REFERENCE TO RELATED APPLICATIONS

This application is based upon and claims the benefit of priority from Japanese Patent Application No. 2016-024096, filed on Feb. 10, 2016; and Japanese Patent Application No. 2016-219857, filed on Nov. 10, 2016, the entire contents of which are incorporated herein by reference.

FIELD

Embodiments described herein relate generally to an ultrasound diagnostic apparatus.

BACKGROUND

Conventionally, ultrasound diagnostic apparatuses have a function of generating and displaying blood flow information from reflected waves of ultrasound by using the Doppler method based on the Doppler effect. Recently, there is a proposed technology of imaging the blood flow at a high rate, a high resolution, and a high frame rate to obtain blood flow information in which clutter components originating from slow-moving tissue that moves slowly are more substantially suppressed than by using the normal Doppler method.

BRIEF DESCRIPTION OF THE DRAWINGS

FIG. 3 is a diagram for explaining processing of an assigning function according to the first embodiment;

FIG. 8 is a diagram for explaining processing of an assigning function according to Modification 3 of the first embodiment; and FIG. 9 is a diagram for explaining processing performed by an ultrasound diagnostic apparatus according to another embodiment.

DETAILED DESCRIPTION

An ultrasound diagnostic apparatus according to an embodiment includes processing circuitry. The processing circuitry causes an ultrasound probe to execute first ultrasound scanning to acquire blood flow information within a first scanning area and causes the ultrasound probe to execute second ultrasound scanning to acquire tissue shape information within a second scanning area. The processing circuitry receives an instruction for changing a flow-velocity value to be displayed in display of the blood flow information. When, because of a change of the flow-velocity value according to the instruction, a time for transmitting/receiving ultrasound per scanning line in the first ultrasound scanning exceeds a transmitting/receiving time before the change, the processing circuitry assigns a time corresponding to the excess to at least one of the first ultrasound scanning and the second ultrasound scanning.

An ultrasound diagnostic apparatus according to the embodiment will be described with reference to the accompanying drawings.

First Embodiment

Figure 1:
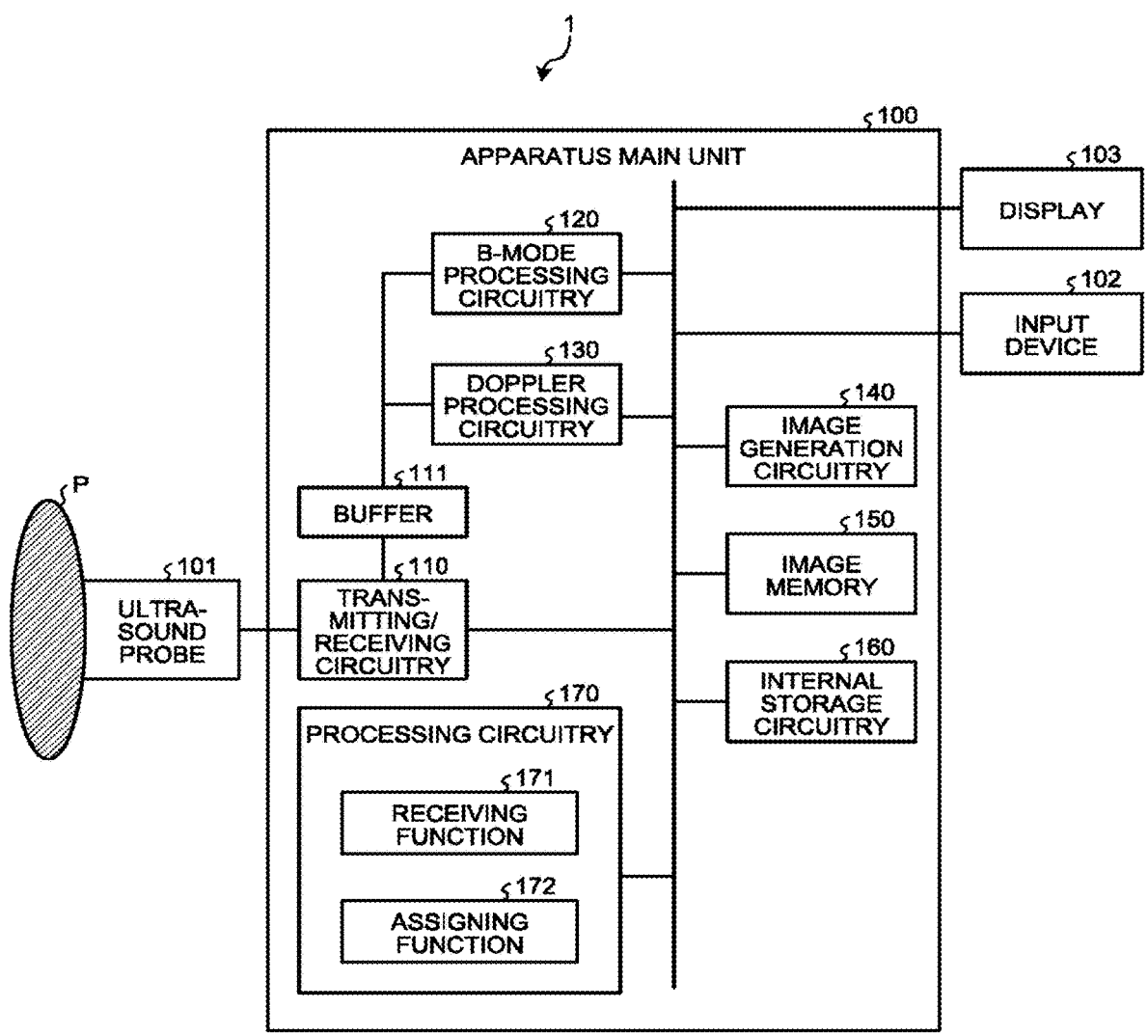
FIG. 1 is a diagram of an exemplary configuration of an ultrasound diagnostic apparatus according to a first embodiment.

FIG. 1 is a block diagram of an exemplary configuration of an ultrasound diagnostic apparatus 1 according to a first embodiment. As illustrated in FIG. 1, an ultrasound diagnostic apparatus 1 according to the first embodiment includes an ultrasound probe 101, an input device 102, a display 103, and an apparatus main unit 100. The ultrasound probe 101, the input device 102 and the display 103 are communicably connected to the apparatus main unit 100. A subject P is not a component of the ultrasound diagnostic apparatus 1.

The ultrasound probe 101 transmits and receives ultrasound. For example, the ultrasound probe 101 includes multiple piezoelectric transducers. The piezoelectric transducers generate ultrasound according to a drive signal that is supplied from transmitting/receiving circuitry 110 of the apparatus main unit 100, which will be described below. The multiple piezoelectric transducers of the ultrasound probe 101 receive reflected waves from the subject P and convert the reflected waves into electric signals. The ultrasound probe 101 further includes a matching layer that is provided to the piezoelectric transducers and a backing member that prevents backward propagation of ultrasound from the ultrasound transducers. The ultrasound probe 101 is detachably connected to the apparatus main unit 100.

When ultrasound is transmitted from the ultrasound probe 101 to the subject P, the transmitted ultrasound is sequentially reflected on a surface of discontinuity of acoustic impedance in a body tissue of the subject P and is received as reflected-wave signals by the piezoelectric transducers of the ultrasound probe 101. The amplitude of the received reflected-wave signal depends on the difference in acoustic impedance on the surface of discontinuity on which the ultrasound is reflected. The reflected-wave signals resulting from reflection of the transmitted ultrasound pulses on a surface, such as the blood flow or the cardiac wall, are, because of the Doppler effect, subjected to a frequency shift depending on velocity components of a moving object with respect to the direction in which the ultrasound is transmitted.

A 1D array probe that scans the subject P two-dimensionally, a mechanical 4D probe that scans the subject P three-dimensionally, or a 2D array probe may be used as the ultrasound probe 101 according to the first embodiment.

The input device 102 corresponds to devices, such as a mouse, a keyboard, a button, a panel switch, a touch command screen, a fit switch, a trackball, and a joystick. The input device 102 receives various setting requests from the operator of the ultrasound diagnostic apparatus 1 and transfers the received various setting requests to the apparatus main unit 100.

The display 103 displays a graphical user interface (GUI) for the operator of the ultrasound diagnostic apparatus 1 to input various setting requests with the input device 102 and displays, for example, ultrasound image data that is generated by the apparatus main unit 100.

The apparatus main unit 100 is an apparatus that generates ultrasound image data on the basis of the reflected-wave signals received by the ultrasound probe 101. The ultrasound image data that is generated by the apparatus main unit 100 illustrated in FIG. 1 may be two-dimensional ultrasound image data that is generated on the basis of two-dimensional reflected-wave signals or three-dimensional ultrasound image data that is generated on the basis of three-dimensional reflected-wave signals.

As illustrated in FIG. 1, the apparatus main unit 100 includes the transmitting/receiving circuitry 110, a B-mode processing circuitry 120, Doppler processing circuitry 130, image generation circuitry 140, an image memory 150, internal storage circuitry 160 and processing circuitry 170. The transmitting/receiving circuitry 110, the B-mode processing circuitry 120, The Doppler processing circuitry 130, the image generation circuitry 140, the image memory 150, the internal storage circuitry 160, and the processing circuitry 170 are communicably connected to one another.

The transmitting/receiving circuitry 110 controls transmission and reception of ultrasound performed by the ultrasound probe 101. The transmitting/receiving circuitry 110 includes a pulse generator, a transmission delay circuit and a pulser and supplies a drive signal to the ultrasound probe 101. The pulse generator repeatedly generates a rate pulse for forming transmission ultrasound at a given repetition frequency. The transmission delay circuit focuses the ultrasound that is generated from the ultrasound probe 101 into a beam shape and assigns delay times for the respective piezoelectric transducers necessary to determine transmission directionality to the rate pulses generated by the pulse generator, respectively. The pulser applies a drive signal (drive pulse) to the ultrasound probe 101 at a timing based on a rate pulse. In other words, the transmission delay circuit freely changes the delay time assigned to each rate pulse, thereby adjusting the transmission direction of ultrasound that is transmitted from the surface of the piezoelectric transducers.

The transmitting/receiving circuitry 110 has a function enabling an instantaneously change of the transmission frequency, the transmission drive voltage, etc., in order to execute a given scanning sequence according to an instruction from the processing circuitry 170, which will be described below. Particularly, a change of the transmission drive voltage is implemented by a linear-amplifier oscillating circuit that is able to switch the value instantaneously or a mechanism that electrically switches between multiple power units.

The transmitting/receiving circuitry 110 further includes an amplifier circuit, an analog/digital (A/D) converter, a receiving delay circuit, an adder and a quadrature detection circuit and performs various processes on the reflected-wave signals received by the ultrasound probe 101 to generate reflected-wave data. The amplifier circuit amplifies the reflected-wave signal per channel to perform gain correction processing. The A/D converter performs A/D conversion on the reflected-wave signal having been subjected to the gain correction. The receiving delay circuit assigns a receiving delay time necessary to determine the receiving directionality to the digital data. The adder performs addition of the reflected-wave signal to which the receiving delay time has been assigned by the receiving delay circuit. The addition performed by the adder enhances the reflection components from the direction corresponding to the receiving directionality of the reflected-wave signal.

The quadrature detection circuit converts the output signal of the adder into a common-mode signal (in-phase (I) signal) and a quadrature signal (quadrature-phase (Q) signal). The quadrature detection circuit stores the I signal and the Q signal (hereinafter, an IQ signal) as reflected-wave data in a buffer 111. The quadrature detection circuit may convert the output signal of the adder into a radio frequency (RF) signal and then store the RF signal in the buffer 111. An IQ signal and an RF signal are signals containing phase information (reception signals). The reflected-wave data that is output by the transmitting/receiving circuitry 110 may be referred to as a reception signal herein.

The buffer 111 is a buffer that temporarily stores the reflected-wave data (IQ signal) that is generated by the transmitting/receiving circuitry 110. Specifically, the buffer 111 stores IQ signals corresponding to few frames or IQ signals corresponding to few volumes. For example, the buffer 111 is a first-in/first-out (FIFO) memory that stores IQ signals corresponding to a given number of frames. For example, when the transmitting/receiving circuitry 110 generates a new IQ signal corresponding to one frame, the buffer 111 discards the IQ signal corresponding to one frame that is generated at the oldest time and stores the generated new I/Q signal corresponding to one frame. The buffer 111 is communicably connected to each of the transmitting/receiving circuitry 110, the B-mode processing circuitry 120, and the Doppler processing circuitry 130.

The transmitting/receiving circuitry 110 is able to generate sets of reflected-wave data with respect to multiple receiving focuses from the reflected-wave signals of the respective piezoelectric transducers that are obtained by one transmission of ultrasound beams. In other words, the transmitting/receiving circuitry 110 is a circuit that is able to perform parallel and simultaneous reception processing. It is possible to carry out the first embodiment even when the transmitting/receiving circuitry 110 is not able to execute the parallel and simultaneous reception processing.

The B-mode processing circuitry 120 and the Doppler processing circuitry 130 are signal processing units that perform various types of signal processing on the reflected-wave data that the transmitting/receiving circuitry 110 generates from the reflected-wave signals. The B-mode processing circuitry 120 performs, for example, logarithmic amplification, envelope detection processing and logarithmic compression on the reflected-wave data (IQ signal) that is read from the buffer 111 to generate data (B-mode data) where the signal intensity at many points is expressed by the level of brightness.

The B-mode processing circuitry 120 is able to change the frequency band subjected to imaging by changing the detected frequency through filtering. The use of the filtering function of the B-mode processing circuitry 120 enables execution of harmonic imaging, such as contrast harmonic imaging (CHI) or tissue harmonic imaging (THI).

The use of the filtering function of the B-mode processing circuitry 120 also enables the ultrasound diagnostic apparatus 1 according to the first embodiment to perform tissue harmonic imaging (THI).

When performing harmonic imaging, such as CHI or THI, the B-mode processing circuitry 120 is able to extract harmonic components by using a method different from the above-described method using filtering. In harmonic imaging, the amplitude modulation (AM) method, the phase modulation (PM) method, and an imaging method referred to as the AMPM method that is the combination of the AM method and the PM method are performed. In the AM method, the PM method and the AMPM method, ultrasound transmission is performed for multiple times at different amplitudes and phases with respect to the same scanning line. Accordingly, the transmitting/receiving circuitry 110 generates and outputs multiple sets of reflected-wave data (reception signals) on each scanning line. The B-mode processing circuitry 120 performs addition and subtraction of multiple sets of reflected-wave data (received signals) of each scanning line according to the modulation method to extract harmonic components. The B-mode processing circuitry 120 then performs envelope detection processing, etc., on the reflected-wave data (reception signal) on the harmonic components to generate B-mode data.

The Doppler processing circuitry 130 analyzes the frequency of the reflected-wave data that is read from the buffer 111 to generate data (Doppler data) obtained by extracting kinetic information on a moving object within a scanning area based on the Doppler effect. Specifically, the Doppler processing circuitry 130 generates Doppler data obtained by estimating, as kinetic information on the moving object, an average velocity, an average disturbance value, and an average power value at each of multiple sample points. The Doppler processing circuitry 130 according to the first embodiment generates, as the kinetic information of the blood flow (blood flow information), Doppler data obtained by estimating an average velocity of the blood flow, an average disturbance value of the blood flow, and an average power value of the blood flow at each of multiple sample points.

By using the above-described function of the Doppler processing circuitry 130, the ultrasound diagnostic apparatus 1 according to the first embodiment is able to execute the color Doppler also referred to as the color flow mapping (CFM). In CFM, ultrasound is transmitted and received for multiple times on multiple scanning lines. In CFM, moving target indicator (MTI) filtering is performed on a data stream with respect to the same position to suppress signals originating from still tissue or slow-moving tissue and extract signals originating from the blood flow. In CFM, blood flow information, such as the blood-flow velocity, blood-flow disturbance and blood-flow power, is estimated from the blood flow signals. The image generation circuitry 140 generates ultrasound image data (color Doppler image data) in which the distribution of the result of estimation is two-dimensionally displayed in color. The display 103 displays the color Doppler image data.

In general, a Butterworth-type infinite impulse response (IIR) filter, a polynomial regression filter or a filter where coefficients are fixed is used as the MTI filter. On the other hand, the Doppler processing circuitry 130 according to the first embodiment uses an adaptive MTI filter that varies the coefficients according to an input signal as the MTI filter. Specifically, the Doppler processing circuitry 130 according to the first embodiment uses a filter referred to as the "Eigenvector Regression Filter" as the MTI filter. Hereinafter, an "Eigenvector Regression Filter" that is an adaptive MII filter using eigenvectors is referred to as the "eigenvector MTI filter".

The eigenvector MTI filter calculates eigenvectors from a correlation matrix and, from the calculated eigenvectors, coefficients used for clutter component suppression processing. This method employs a method used for main component analysis, Karhunen-Loeve transform, and the eigenspace method.

The Doppler processing circuitry 130 according to the first embodiment using the eigenvector MTI filter calculates a correlation matrix of a scanning area from a data stream of sequential reflected-wave data with respect to the same position (the same sample point). For example, the Doppler processing circuitry 130 calculates eigenvalues of the correlation matrix and eigenvectors corresponding to the eigenvalues. The Doppler processing circuitry 130 calculates, for example, a matrix where the ranks of the matrix where each eigenvector is arranged according to the magnitude of each eigenvalue as a filter matrix that suppresses the clutter components. The Doppler processing circuitry 130 determines the number of main components to be reduced, i.e., the value of the number of ranks to be cut, according to a pre-set value or a value specified by the operator. When tissue of, for example, the heart or a blood vessel, whose transfer velocity changes with time according to the beats is contained in the scanning area, it is preferable that the value of the number of ranks to be cut be adaptively determined from the magnitude of the eigenvalues. In other words, the Doppler processing circuitry 130 changes the number of main components to be reduced according to the magnitude of the eigenvalues of the correlation matrix. In the first embodiment, the Doppler processing circuitry 130 changes the number of ranks to be reduced according to the magnitude of the eigenvalues.

By using the filter matrix and from the data stream of sequential reflected-wave data with respect to the same position (the same sample point), the Doppler processing circuitry 130 outputs a data stream from which blood-flow signals originating from the blood flow in which clutter components are suppressed are extracted. The Doppler processing circuitry 130 estimates blood flow information by performing arithmetic operations, such as autocorrelation operations, using the output data and outputs the estimated blood flow information as the Doppler data.

The image generation circuitry 140 generates ultrasound image data from the data that is generated by the B-mode processing circuitry 120 and the Doppler processing circuitry 130. The image generation circuitry 140 generates, from the two-dimensional B-mode data that is generated by the B-mode processing circuitry 120, two-dimensional B-mode image data where the intensity of the reflected waves is expressed in brightness. The image generation circuitry 140 generate, from the two-dimensional Doppler data that is generated by the Doppler processing circuitry 130, two-dimensional Doppler image data where the blood-flow information is imaged. The two-dimensional Doppler image data is velocity image data, disturbance image data, power image data, or image data that is a combination of these sets of data. The image generation circuitry 140 generates, as the Doppler image data, color Doppler image data where the blood information is displayed in color or Doppler image data where one set of blood flow information is displayed in grayscale.

In general, the image generation circuitry 140 converts a scanning-line signal stream of ultrasound scanning into a scanning-line signal stream of the video format represented by, for example, TV (scan conversion) to generate ultrasound image data for display. Specifically, the image generation circuitry 140 performs coordinate conversion according to the mode of ultrasound scanning performed by the ultrasound probe 101 to generate ultrasound image data for display. The image generation circuitry 140 performs various types of image processing such as, in addition to scan conversion, image processing of regenerating an image having an average value of brightness by using multiple image frames after the scan conversion (smoothing) and image processing using a differential filter in the image (edge enhancement). The image generation circuitry 140 synthesizes character information of various parameters, a scale, and body signs, etc., into the ultrasound image data.

In other words, the B-mode data and the Doppler data are ultrasound image data before scan conversion processing and the data generated by the image generation circuitry 140 is ultrasound image data for display after the scan conversion processing. The B-mode data and the Doppler data are also referred to as raw data. The image generation circuitry 140 generates two-dimensional ultrasound image data for display from the two-dimensional ultrasound image data before scan conversion processing.

Furthermore, the image generation circuitry 140 performs coordinate transform on the three-dimensional B-mode data that is generated by the B-mode processing circuitry 120. The image generation circuitry 140 performs coordinate transform on the three-dimensional Doppler data, which is generated by the Doppler processing circuitry 130, to generate three-dimensional Doppler image data.

Furthermore, in order to generate various types of two-dimensional image data for displaying the volume data on the display 103, the image generation circuitry 140 performs rendering on the volume data. The rendering performed by the image generation circuitry 140 is, for example, processing of performing multi planer planar reconstruction (MPR) to generate MPR image data from the volume data. Furthermore, the rendering performed by the image generation circuitry 140 is, for example, volume rendering (VR) to generate two-dimensional image data that reflects three-dimensional information.

The image memory 150 is a memory that stores image data for display that is generated by the image generation circuitry 140. The image memory 150 is also able to store the data that is generated by the B-mode processing circuitry 120 and the Doppler processing circuitry 130. It is possible for the operator to call, for example, after diagnosis, the B-mode data and Doppler data stored in the image memory 150, and the B-mode data and the Doppler data turn into ultrasound image data for display via the image generation circuitry 140. The image memory 150 is also able to store the reflected-wave data that is output by the transmitting/receiving circuitry 110.

The internal storage circuitry 160 stores control programs for performing ultrasound transmission/reception, image processing, and display processing, diagnostic information (such as patent IDs and opinions of doctors), and various types of data, such as diagnostic protocols and various body signs. The internal storage circuitry 160 is also used to, for example, keep the image data stored in the image memory 150, as required. The data stored in the internal storage circuitry 160 is transferrable to external devices via an interface (not shown). The internal storage circuitry 160 is also able to store data that is transferred from external devices via an interface (not shown).

The processing circuitry 170 controls the entire processing performed by the ultrasound diagnostic apparatus 1. Specifically, the processing circuitry 170 controls the processing performed by the transmitting/receiving circuitry 110, the B-mode processing circuitry 120, the Doppler processing circuitry 130, and the image generation circuitry 140 according to various setting requests that are input by the operator via the input device 102 and various control programs and various types of data that are read from the internal storage circuitry 160. The processing circuitry 170 further performs control such that the display 103 displays ultrasound image data for display that is stored in the image memory 150 and the internal storage circuitry 160.

For example, the processing circuitry 170 controls the ultrasound probe 101 via the transmitting/receiving circuitry 110 to control ultrasound scanning. In general, In CFM, the color Doppler image data that is blood-flow image data and the B-mode image data that is tissue image data are displayed together. In order for the display, the processing circuitry 170 causes the ultrasound probe 101 to execute first ultrasound scanning to acquire information on the blood flow within a first scanning area. The first ultrasound scanning is, for example, ultrasound scanning for acquiring color Doppler image data in a Doppler mode. The processing circuitry 170 further causes the ultrasound probe 101 to execute, together with the first ultrasound scanning, second ultrasound scanning for acquiring information on the shape of tissue (tissue shape information) within a second scanning area. The second ultrasound scanning is, for example, ultrasound scanning for acquiring B-mode image data in a B mode.

The processing circuitry 170 implements an receiving function 171 and an assigning function 172. Each of the processing functions implemented by the receiving function 171 and the assigning function 172 that are components of the processing circuitry 170 is, for example, recorded in the internal storage circuitry 160 in a mode of a program executable by, for example, a computer. The processing circuitry 170 is a processor that implements the function corresponding to each of the programs by reading each of the programs from the internal storage circuitry 160 and executing the program. In other words, the receiving function 171 is a function implemented by the processing circuitry 170 by reading the program corresponding to the receiving function 171 from the internal storage circuitry 160 and executing the program. The assigning function 172 is a function implemented by the processing circuitry 170 by reading the program corresponding to the assigning function 172 from the internal storage circuitry 160 and executing the program. In other words, the processing circuitry 170 having read each of the programs has each of the functions illustrated in the processing circuitry 170 in FIG. 1. The processing functions executed by the receiving function 171 and the assigning function 172, respectively, will be described below.

The first embodiment has been described as one where the single processing circuitry 170 implements each of the above-described processing functions; however, a processing circuit may be configured by combining multiple independent processors and the processors may execute the programs, respectively, to implement the functions.

The word "processor" used in the above descriptions refers to a central processing unit (CPU), a graphics processing unit (GPU), or a circuit, such as an application specific integrated circuit (ASIC), a programmable logic device (such as a simple programmable logic device (SPLD)), a complex programmable logic device (CPLD), or a field programmable gate array (FPGA). The processor implements the functions by reading and executing the programs saved in the storage circuit. Instead of saving the programs in the internal storage circuitry 160, the programs may be configured to be directly incorporated in the circuit of the processor. In this case, the processor implements the functions by reading and executing the programs incorporated in the circuit. Furthermore, each processor of the first embodiment is not limited to a case where each processor is configured as a single circuit. Multiple independent circuits may be combined to configure a single processor to implement the functions. Alternatively, multiple components in each drawing may be integrated into one processor to implement the functions.

The ultrasound diagnostic apparatus 1 according to the first embodiment images the blood blow at a high-speed, a high resolution, and a high frame rate, thereby executing the Doppler-mode ultrasound scanning to obtain blood flow information in which clutter components are more substantially suppressed than by using the normal Doppler method. Specifically, the first ultrasound scanning performed in the first embodiment is executed by repeating a scanning mode enabling acquisition of reflected-wave data with respect to the same position over multiple frames through ultrasound transmission/reception in a scanning area that is formed of multiple scanning lines. More specifically, the first ultrasound scanning performed in the first embodiment is executed by repeating a scanning mode where ultrasound transmission/reception in a scanning area formed of multiple scanning lines is performed once with respect to each of the scanning lines. The scanning mode is the same scanning mode as that of the second ultrasound scanning performed in the normal B mode and is the same scanning mode as that taken by CFM to increase the frame rate.

Figure 2:
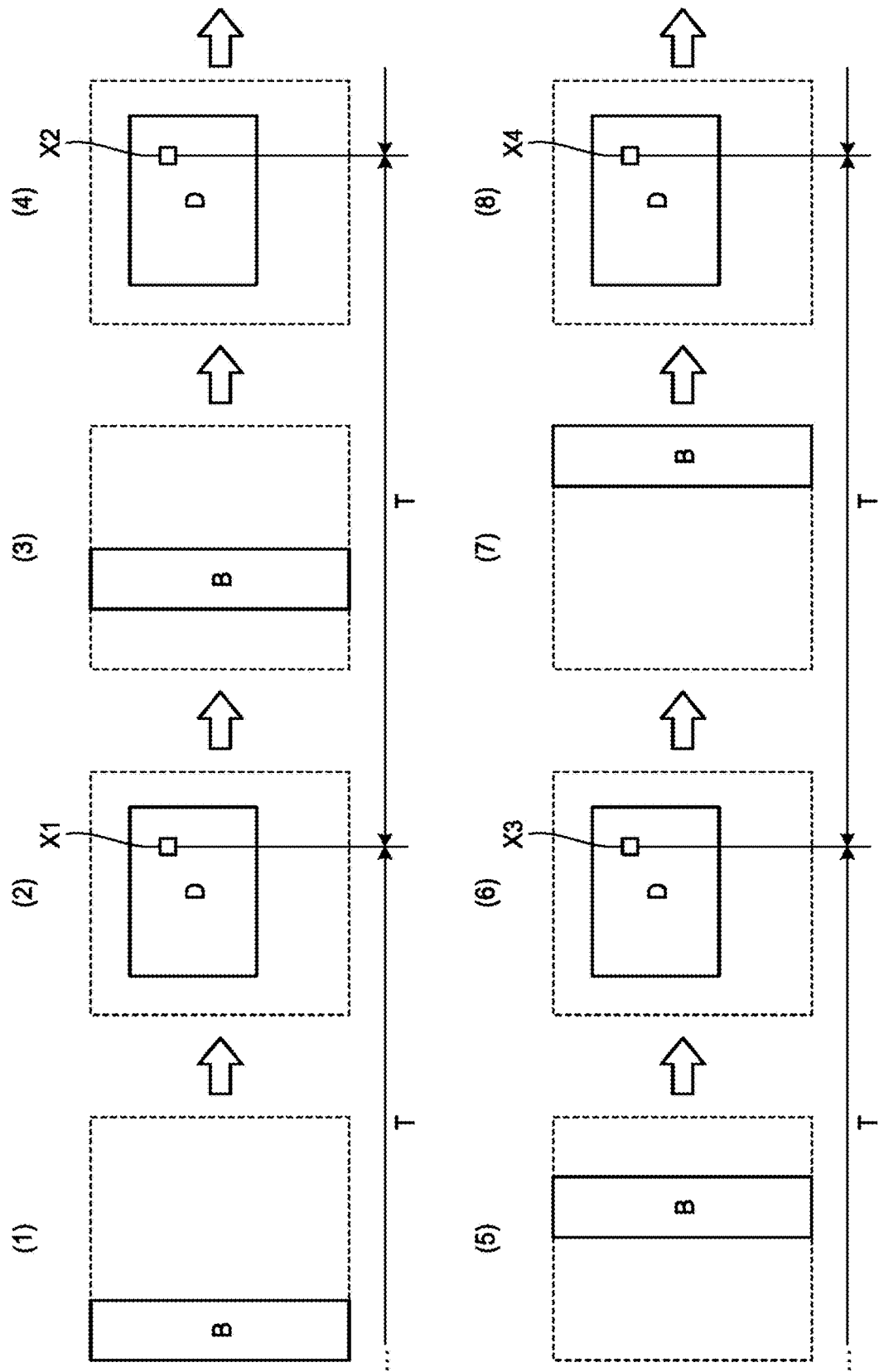
FIG. 2 is a diagram of an exemplary Doppler-mode ultrasound scanning according to the first embodiment.

FIG. 2 is a diagram of exemplary Doppler-mode ultrasound scanning according to the first embodiment. In the example illustrated in FIG. 2, the processing circuitry 170 of the ultrasound diagnostic apparatus 1 causes the ultrasound probe 101 to execute, as the second ultrasound scanning, ultrasound scanning on each of multiple divided areas obtained by dividing a second scanning area during the first ultrasound scanning though time sharing. In other words, the processing circuitry 170 performs the second ultrasound scanning partly during the first ultrasound scanning and completes the second ultrasound scanning for one frame within the period in which the first ultrasound scanning for few frames is performed. This scanning mode allows the ultrasound diagnostic apparatus 1 according to the first embodiment to set ultrasound transmitting/receiving conditions of the respective first ultrasound scanning and second ultrasound scanning independently of each other. For example, the ultrasound diagnostic apparatus 1 according to the first embodiment is able to cause the second ultrasound scanning to be executed under the condition according to THI. In other words, the above-described filtering enables execution of the second ultrasound scanning under the ultrasound transmitting/receiving condition for performing THI. Furthermore, it is possible to execute the second ultrasound scanning under an ultrasound transmitting/receiving condition for performing THI based on the imaging method of performing ultrasound transmission at multiple rates with respect to one scanning line, such as the above-described the AM method, the PM method, the AMPM or a method using combination tone components. The processing circuitry 170 is an exemplary controller. The controller causes the ultrasound probe 101 to execute the first ultrasound scanning to acquire information on the blood flow within the first scanning area and causes the ultrasound probe 101 to execute, as the second ultrasound scanning to acquire information on the shape of tissue within the second scanning area, ultrasound scanning on each of multiple divided areas obtained by dividing the second scanning area during the first ultrasound scanning though time sharing. In other words, the processing circuitry 170 causes the ultrasound probe 101 to execute the first ultrasound scanning to acquire information on the blood flow within the first scanning area and causes the ultrasound probe 101 to execute the second ultrasound scanning to acquire information on the shape of tissue within the second scanning area during the first ultrasound scanning though time sharing.

With reference to FIG. 2, an example of the above-described processing will be described. For example, the processing circuitry 170 divides the second scanning area into four divided areas (first divided area to fourth divided area) according to an instruction from the operator or information that is set initially, etc. The dotted rectangle illustrated in FIG. 2 represents the whole second scanning area that is scanned by using the B-mode transmitting/receiving condition and "B" represented in FIG. 2 denotes a divided area that is scanned though time sharing. For example, the processing circuitry 170 causes ultrasound scanning (second ultrasound scanning) on the divided area denoted with "B" out of the whole second scanning area to be executed. Furthermore, "D" represented in FIG. 2 denotes a first scanning area to be scanned by using the color-Doppler mode transmitting/receiving condition. For example, the processing circuitry 170 causes the ultrasound scanning (first ultrasound scanning) on the area denoted with "D" to be executed by using the above-described high frame rate. In other words, in the first ultrasound scanning exemplified in FIG. 2, ultrasound transmitting/receiving is performed once with respect to each scanning line, not as in the case of the general color Doppler method where ultrasound is transmitted for multiple times in the same direction and the reflected-wave is received for multiple times. The processing circuitry 170 performs, as first ultrasound scanning, ultrasound transmitting/receiving once with respect to each of the multiple scanning lines that form the first scanning area to execute ultrasound scanning based on the method of acquiring blood-flow information by using reflected-waves for multiple frames (high frame-rate method). FIG. 2 illustrates the case where the scanning area "D" on which the first ultrasound scanning is performed is smaller than the whole scanning area (dotted area) on which the second ultrasound scanning is performed; however, embodiments are not limited to this. For example, the scanning area "D" on which the first ultrasound scanning is performed may be larger than the whole scanning area (dotted area) on which the second ultrasound scanning is performed, or both the areas may have the same size.

First of all, the processing circuitry 170 causes ultrasound scanning on a first divided area (see (1) in FIG. 2) to be executed as the second ultrasound scanning and causes the first ultrasound scanning on a first scanning area (for one frame) to be executed (see (2) in FIG. 2). The processing circuitry 170 then causes ultrasound scanning on a second divided area to be executed as the second ultrasound scanning (see (3) in FIG. 2) and causes the first ultrasound scanning on the first scanning area (for one frame) to be executed (see (4) in FIG. 2). The processing circuitry 170 then causes ultrasound scanning on a third divided area to be executed as the second ultrasound scanning (see (5) in FIG. 2) and causes the first ultrasound scanning on the first scanning area (for one frame) to be executed (see (6) in FIG. 2). The processing circuitry 170 then causes ultrasound scanning on a fourth divided area to be executed as the second ultrasound scanning (see (7) in FIG. 2) and causes the first ultrasound scanning on the first scanning area (for one frame) to be executed (see (8) in FIG. 2). As described above, the processing circuitry 170 causes the second ultrasound scanning on each of the multiple divided areas to be executed during the first ultrasound scanning though time sharing.

The processing circuitry 170 sets equal intervals at which the first ultrasound scanning is performed. In other words, a "point X" on a "scanning line" within the first scanning area is scanned once in each of the sets of first ultrasound scanning illustrated in (2), (4), (6) and (8) in FIG. 2 and the scanning intervals are controlled to be constant times "T". Specifically, the processing circuitry 170 sets equal the times required for the respective sets of divided scanning performed in the second ultrasound scanning and keeps equal the intervals at which the first ultrasound scanning is performed. For example, the processing circuitry 170 performs control such that the times required for the sets of divided scanning in the second ultrasound scanning performed as illustrated in (1), (3), (5) and (7) in FIG. 2 are equal to one another. The processing circuitry 170 keeps equal the size of the divided areas obtained by dividing the second scanning area, the number of scanning lines, and the density and depth of scanning lines.

In the example illustrated in FIG. 2, tissue image data (tissue shape information) is generated each time the second ultrasound scanning on each of the first to fourth divided areas "B" is performed. For example, when the second ultrasound scanning on the first divided area "B" is performed as illustrated in (1) in FIG. 2, tissue image data (image) corresponding to the first divided area "B" is generated. When the second ultrasound scanning on the second divided area "B" is performed as illustrated in (3) in FIG. 2, tissue image data (image) corresponding to the second divided area "B" is generated. When the second ultrasound scanning on the third divided area "B" is performed as illustrated in (5) in FIG. 2, tissue image data (image) corresponding to the third divided area "B" is generated. When the second ultrasound scanning on the fourth divided area "B" is performed as illustrated in (7) in FIG. 2, tissue image data (image) corresponding to the fourth divided area "B" is generated. Furthermore, when the second ultrasound scanning on the first divided area "B" is performed, tissue image data corresponding to the first divided area "B" is generated (updated), and, when the second ultrasound scanning on the second divided area "B" is performed, tissue image data corresponding to the second divided area "B" is generated (updated). As described above, the processing circuitry 170 updates the tissue image data on each of the divided areas "B" each time the second ultrasound scanning on each of the divided areas "B" is performed. When THI based on the imaging method of performing ultrasound transmission at multiple rates with respect to one scanning line is performed, the number of times for which ultrasound transmission to acquire a reception signal for one frame is performed increases and accordingly, compared to the normal B-mode imaging or the case where THI is performed through filtering, it is necessary to increase the number of divided areas of the second scanning area. For example, when the PM method is performed, the number of divided areas of the second scanning area is changed from four to eight.

The image according to the moving object information (e.g., blood flow image) is generated by performing filtering (for example, filtering using the eigenvector MTI filter) on the data stream of sets of reflected-wave data with respect to the same position in the multiple frames. The data length of the data stream used to output a set of moving object information may be set (changed) freely. Furthermore, it is possible to overlap the data stream used to output the moving object information in the previous phase and the data stream used to output the moving object information in the next time phase with each other and the number of data streams to overlap may be set (changed) freely.

For example, the case with respect to FIG. 2 will be described where the data length of the data stream is set at "4" and the number of data streams to overlap between frames to be displayed is set at "2". In this case, for example, when the first ultrasound scanning illustrated in (2), (4), (6) and (8) in FIG. 2 is performed, filtering is performed on the data streams with respect to the position X1 in (2), the position X2 in (4), the position X3 in (6) and the position X4 in (8) and accordingly moving object information with respect to the position X of the first frame is generated. Generating moving object information with respect to each position within the scanning area generates moving object information on the first frame. When the first ultrasound scanning is further executed twice, filtering is performed on the four sets of data streams with respect to the position X including the position X3 in (6) and the position X4 in (8) and accordingly moving object information with respect to the position X of the second frame is generated. In this manner, each time the first ultrasound scanning is performed for the number of times corresponding to the number of data streams to overlap "2", the processing circuitry 170 performs filtering on the data stream of the data length "4" to generate moving object information with respect to each frame.

As described above, the ultrasound diagnostic apparatus 1 according to the first embodiment images the blood flow at a high resolution and a high frame rate, thereby executing ultrasound scanning according to the high-frame rate method with which a blood flow image where clutter components are more significantly suppressed than by using the normal Doppler method. In other words, the ultrasound diagnostic apparatus 1 executes the second ultrasound scanning on each of the divided areas through time sharing during the first ultrasound scanning where transmission and reception of ultrasound are performed once on each of the scanning lines forming the scanning area, thereby generating blood flow images and tissue images at a high resolution and a high frame rate. Furthermore, the ultrasound diagnostic apparatus 1 performs filtering using the eigenvector MTI filter on the data streams with respect to the same position of the multiple frames, thereby generating a blood flow image where clutter components are significantly suppressed.

In the above-described Doppler-mode ultrasound filtering, however, for example, the image quality of the displayed image may lower with a change of the range of the value of flow velocity (hereinafter, also referred to as the "flow-velocity range"). For example, upon receiving an instruction for lowering the upper limit of the flow-velocity range from the operator, the processing circuitry 170 lowers the upper limit of the flow-velocity range by lowering the pulse repetition frequency (PRF) of the first ultrasound scanning. With the PRF lowering, the scanning interval "T" for the first ultrasound scanning extends (see FIG. 2) and accordingly the scanning intervals for the second ultrasound scanning also extend. For this reason, the update rate at which the tissue image data with respect to each divided area "B" lowers. When the update rate lowers, for example, in the example illustrated in FIG. 2, the update of each of the divided areas from the left to the right becomes prominent, which looks like a wave from the left to the right. As described above, the image quality of the displayed image may lower with a change of the range of the flow velocity value.

In order to improve the image quality of the displayed image with a change of the range of the flow velocity value, the ultrasound diagnostic apparatus 1 according to the first embodiment executes each of the following processing functions. Specifically, the ultrasound diagnostic apparatus 1 receives an instruction for changing the range of the flow-velocity value. When the transmitting/receiving time with respect to each scanning line required for display of the range of the flow-velocity value after the change according to the received instruction is longer than the transmitting/receiving time before the change, the ultrasound diagnostic apparatus 1 assigns the time of the difference between the transmitting/receiving times as the time for improving the image quality of the displayed image.

FIG. 1 will be referred back and described. The processing circuitry 170 according to the first embodiment implements the receiving function 171 and the assigning function 172.

The receiving function 171 receives an instruction for changing the range of the flow velocity value to be displayed in display of the blood flow information. For example, the receiving function 171 provides a user interface (UI) enabling a change of the upper limit value of the range of the flow velocity value (flow-velocity range) according to an operation of the input device 102. The receiving function 171 is an exemplary receiving unit. In other words, the processing circuitry 170 receives an instruction for changing the flow velocity value to be displayed in display of the blood flow information.

An exemplary case will be described where a tab on the operation panel of the ultrasound diagnostic apparatus 1 is used as the input device 102. In this case, with respect to the receiving function 171, the direction of turn of the tab is associated with an increase/decrease of the upper limit value and the amount of turn of the tab is associated with the amount of a change of the upper limit value. When the operator turns the tab in the direction to increase the upper limit value, the receiving function 171 receives the turn as an instruction for increasing the upper limit value corresponding to the amount of turn of the tab. Accordingly, the processing circuitry 170 increases the upper limit value of the flow-velocity range according to the amount of turn of the tab. When the operator turns the tab in the direction to decrease the upper limit value, the receiving function 171 receives the turn as an instruction for decreasing the upper limit value according to the amount of turn of the tab. Accordingly, the processing circuitry 170 decreases the upper limit value of the flow-velocity range according to the amount of turn of the tab.

The first embodiment will be described as the case where the receiving function 171 receives an instruction for increasing the upper limit value of the flow-velocity range; however, embodiments are not limited to this. For example, the receiving function 171 does not necessarily accept an instruction for increasing the upper limit value of the flow-velocity range. In this case, even when the operator turns the tab in the direction to increase the upper limit value, the receiving function 171 does not accept the turn as an instruction and accordingly the processing circuitry 170 does not increase (change) the upper limit value.

The UI provided by the receiving function 171 is not limited to the above-described example. Any technology for changing the parameter according to an instruction of the operator may be used. For example, the receiving function 171 may change the upper limit value of the range of the flow-velocity value by operating not a tab but a button.

In the first ultrasound scanning, when the time for transmitting/receiving ultrasound per scanning line required to display the range of the flow velocity value after a change according to an instruction received by the receiving function 171 is longer than the transmitting/receiving time before the change, the assigning function 171 assigns the time of the difference between the transmitting/receiving time after the change and the transmitting/receiving time before the change to at least one of the first ultrasound scanning and the second ultrasound scanning. In other words, when the flow velocity value is changed according to an instruction and accordingly the ultrasound transmitting/receiving time per scanning line in the first ultrasound scanning exceeds the transmitting/receiving time before the change, the processing circuitry 170 assigns the time of the excess to at least one of the first ultrasound scanning and the second ultrasound scanning. For example, when the receiving function 171 receives an instruction for lowering the upper limit value of the flow-velocity range, the assigning function 172 assigns the time of the difference (time of excess) to the time for extending the length of the divided area in the orientation direction. The assigning function 172 is an exemplary assigning unit.

FIG. 3 is a diagram for explaining the processing performed by the assigning function 172 according to the first embodiment. FIG. 3 exemplifies that the scanning conditions of the first ultrasound scanning (Doppler-mode scanning) and the second ultrasound scanning (B-mode scanning) are changed with a change of the flow-velocity range. The drawings on the left among the upper, intermediate and lower diagrams in FIG. 3 represent a whole second scanning area 10 and a whole divided area 11 in the second ultrasound scanning that is executed by the ultrasound probe 101. The diagrams on the right represent a first scanning area 12 in the first ultrasound scanning that is executed by the ultrasound probe 101.

As illustrated in the upper drawings in FIG. 3, before the flow-velocity range is changed, the processing circuitry 170 performs the second ultrasound scanning on the divided area 11 and performs the first ultrasound scanning on the first scanning area 12. The length of the divided area 11 in the orientation direction is "w1". The transmitting/receiving time per scanning line in the first scanning area 12 is "t1".

When the receiving function 171 receives an instruction for lowering the upper limit value of the flow-velocity range, the processing circuitry 170 lowers the PRF of the first ultrasound scanning to lower the upper limit value of the flow-velocity range. With the PRF lowering, the assigning function 172 calculates "t2" longer than "t1" as the time for transmitting/receiving ultrasound per scanning line required to display the range of the flow velocity value that is changed according to the instruction (see the intermediate diagrams in FIG. 3).

Even when the scanning condition of the first ultrasound scanning is changed to the transmitting/receiving time "t2", the first scanning area 12 that is displayed as the blood flow image is not changed. For this reason, the time of the part extended from the transmitting/receiving time "t1" among the transmitting/receiving time "t2" serves as a "latency time" where imaging is not performed practically.

To deal with this, the assigning function 172 assigns the latency time to the B-mode scanning as illustrated in the lower drawings in FIG. 3. For example, the assigning function 172 assigns the latency time to the time for extending the length "w1" of the divided area 11 in the orientation direction. Accordingly, the processing circuitry 170 executes the second ultrasound scanning on a divided area 13 resulting from extension of the length in the orientation direction from "w1" to "w2".

Specifically, first of all, the assigning function 172 calculates a latency time $\Delta T[s]$ that occurs to scan the first scanning area 12 once, by using the following Equation (1) where NumRaster corresponds to the number of lines (rasters) contained in the first scanning area 12.

$$\Delta T[s]=(t2-t1)\times\text{NumRaster} \quad (1)$$

The assigning function 172 then calculates the number of scanning lines NumAddRaster on which the receiving/transmitting can be performed during the latency time ΔT[s] in the second ultrasound scanning, by using the following Equation (2) where Round corresponds to the number of scanning lines contained in each divided area 11 and TimeB corresponding to the time of scanning each divided area 11. The solution of Equation (2) is rounded to the closest whole number.

$$\text{NumAddRaster}=\text{Round}(\Delta T/\text{TimeB}) \quad (2)$$

In this manner, from the latency time ΔT, the assigning function 172 calculates the number of scanning lines NumAddRaster that can be added in the second ultrasound scanning. For example, the processing circuitry 170 adds the number of scanning lines that is calculated by the assigning function 172 to the divided area 11 to obtain the divided area 13. In the example illustrated in the lower diagrams in FIG. 3, the processing circuitry 170 adds the calculated number of scanning lines without changing the density of scanning lines in the divided area 11 to obtain the divided area 13.

As a result, after the flow-velocity range is changed, the processing circuitry 170 performs the second ultrasound scanning on the divided area 13 having the length "w2" in the orientation direction and performs the first ultrasound scanning in the transmitting/receiving time "t1" per scanning line. Accordingly, the processing circuitry 170 increases the size of each divided area, which makes it possible to increase the update rate of the B-mode scanning.

FIG. 3 exemplifies the case where, with the change of the flow-velocity range, the number of scanning lines in the divided area 11 is changed from "three" to "six (divided area 13)"; however, embodiments are not limited to this. For example, when the result of the calculation according to Equation (2) is "NumAddRaster=1", the number of scanning lines in the divided area 13 is "four", and, when "NumAddRaster=2", the number of scanning lines in the divided area 13 is "five". In other words, the number of scanning lines in the divided area 11 may be increased one by one according to the result of calculation according to Equation (2). When the result of calculation according to Equation (2) is "smaller than 1", even one scanning line may be not necessarily added.

Figure 4:
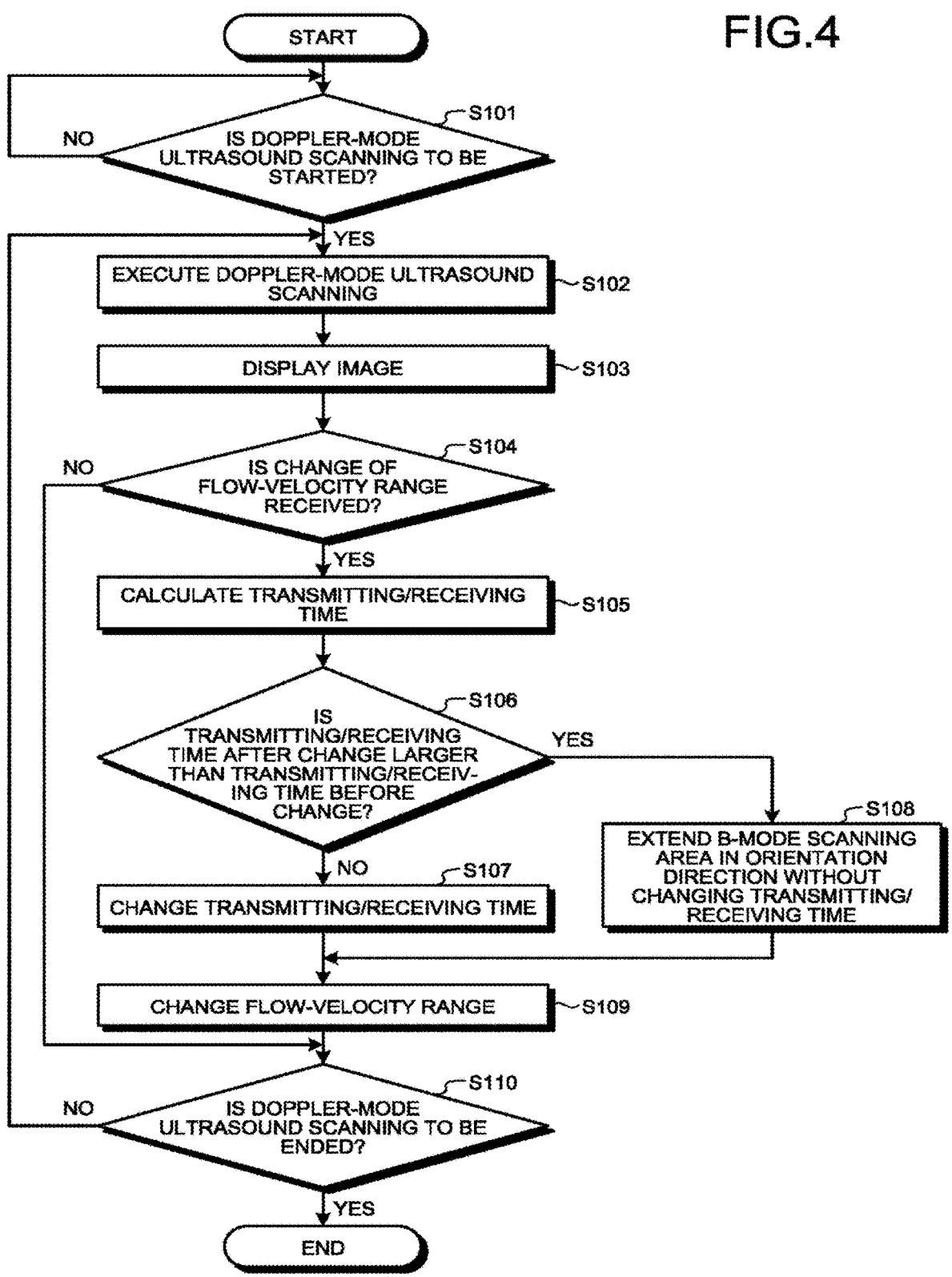
FIG. 4 is a flowchart of a processing procedure performed by the ultrasound diagnostic apparatus according to the first embodiment.

FIG. 4 is a flowchart of a processing procedure performed by the ultrasound diagnostic apparatus 1 according to the first embodiment. The processing procedure illustrated in FIG. 4 is started, for example, when a start instruction for starting the Doppler-mode ultrasound scanning is received from an operator.

At step S101, the processing circuitry 170 determines whether a start instruction for starting the Doppler-mode ultrasound scanning is received. When a start instruction for starting the Doppler-mode ultrasound scanning is received, the processing circuitry 170 starts the process from and after step S102. When NO at step S101, the process from and after step S102 is not started and each of the processing functions of the processing circuitry 170 enters a standby state.

When YES at step S101, the processing circuitry 170 executes the Doppler-mode ultrasound scanning at step S102. For example, the processing circuitry 170 controls the transmitting/receiving circuitry 110, the B-mode processing circuitry 120, and the Doppler processing circuitry 130 to control the ultrasound scanning.

At step S103, the processing circuitry 170 displays an image. For example, the processing circuitry 170 displays, on the display 103, an image that is generated by the image generation circuitry 140 on the basis of reflected-wave data that is acquired through the Doppler-mode ultrasound scanning. Specifically, the processing circuitry 170 displays a tissue image and displays a blood-flow image on a specified region of interest (ROI) on the tissue image in a superimposed manner.

At step S104, the receiving function 171 determines whether a change of a flow-velocity range is received. When a change of the flow-velocity range is received, the receiving function 171 executes the process from and after step S105. When NO at step S104, the receiving function 171 moves to the processing at step S110.

When YES at step S104, at step S105, the assigning function 172 calculates a time for transmitting/receiving ultrasound per scanning line required to display the range of the flow velocity value after the change according to the instruction. For example, when the receiving function 171 receives an instruction for changing the flow-velocity range, with the PRF lowering, the assigning function 172 calculates a transmitting/receiving time (transmitting/receiving time after the change) per scanning line "t2" required to display the range of the flow velocity value after the change according to the instruction.

At step S106, the assigning function 172 determines whether the transmitting/receiving time "t2" after the change is larger than the transmitting/receiving time "t1" before the change. When the transmitting/receiving time "t2" after the change is smaller than the transmitting/receiving time "t1" before the change, the assigning function 172 executes the processing at step S107. On the other hand, when the transmitting/receiving time "t2" after the change is larger than the transmitting/receiving time "t1" before the change, the assigning function 172 executes the processing at step S108.

When NO at step S106, at step S107, the processing circuitry 170 changes the transmitting/receiving time. Specifically, the processing circuitry 170 changes the transmitting/receiving time "t1" before the change to the transmitting/receiving time "t2" after the change and changes another parameter contained in the scanning condition of the first ultrasound scanning.

When YES at step S106, at step S108, the assigning function 172 extends the B-mode scanning area (divided area) in the orientation direction without changing the transmitting/receiving time. In other words, the assigning function 172 assigns the time of the difference between the transmitting/receiving time "t1" before the change and the transmitting/receiving time "t2" after the change to the time for increasing the length of the divided area in the orientation direction. Specifically, the assigning function 172 calculates a latency time ΔT from the difference between the transmitting/receiving time "t1" before the change and the transmitting/receiving time "t2" after the change. The assigning function 172 then calculates the number of scanning lines NumAddRaster on which the transmitting/receiving can be performed during the calculated latency time ΔT. The assigning function 172 adds the calculated number of scanning lines to divided area for B-mode scanning to increase the length of the divided area in the orientation direction.

At step S109, the processing circuitry 170 changes the flow-velocity range. For example, the processing circuitry 170 changes the upper limit of the flow-velocity range according to the instruction received by the receiving function 171.

At step S110, the processing circuitry 170 determines whether an end instruction for ending the Doppler-mode ultrasound scanning is received. Upon receiving the instruction for ending the Doppler-mode ultrasound scanning, the processing circuitry 170 ends the processing procedure illustrated in FIG. 4. When No at step S110, the processing circuitry 170 moves to step S102.

As described above, the ultrasound diagnostic apparatus 1 according to the first embodiment receives an instruction for changing the range of the flow-velocity value. When the time for transmitting/receiving ultrasound per scanning line required to display the range of the flow-velocity value after the change according to the received instruction is longer than the transmitting/receiving time before the change, the ultrasound diagnostic apparatus 1 assigns the time of the difference between the transmitting/receiving times to a time for improving the image quality of the displayed image. Accordingly, the ultrasound diagnostic apparatus 1 according to the first embodiment is able to improve the image quality of the displayed image according to the change of the range of the flow-velocity value.

Figure 5:
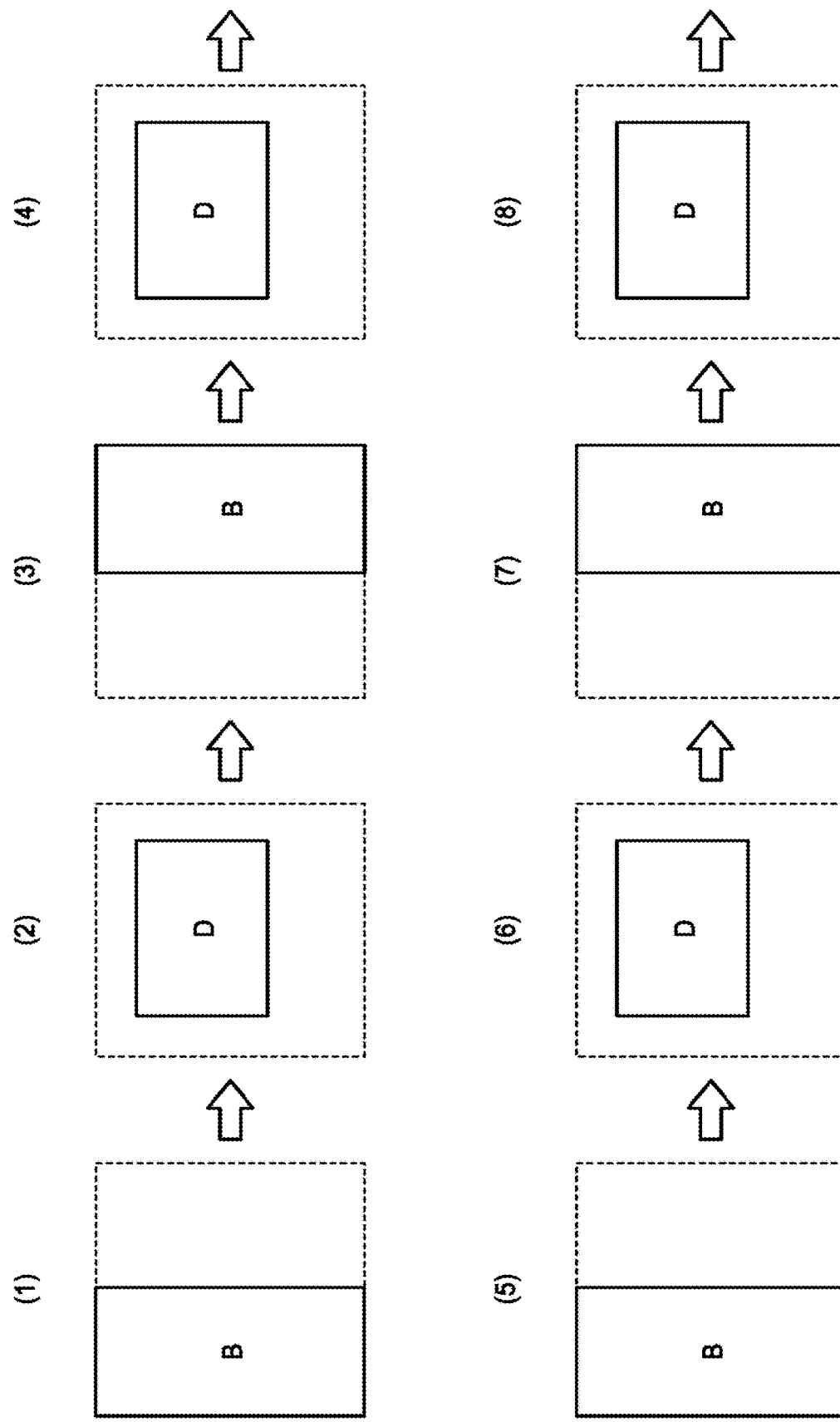
FIG. 5 is a diagram for explaining an effect obtained with the ultrasound diagnostic apparatus according to the first embodiment.

FIG. 5 is a diagram for explaining effects of the ultrasound diagnostic apparatus 1 according to the first embodiment. FIG. 5 exemplifies ultrasound scanning after the issuance of an instruction for lowering the upper limit value of the flow-velocity range in the Doppler-mode ultrasound scanning illustrated in FIG. 2.

As illustrated in FIG. 5, in the ultrasound diagnostic apparatus 1, when an instruction for lowering the upper limit value of the flow-velocity range is issued and the transmitting/receiving time after the change according to the instruction is longer than the transmitting/receiving time before the change, the assigning function 172 assigns the time of the difference between the transmitting/receiving times to the time for increasing the length of the divided area in the orientation direction. In the example illustrated in FIG. 5, the processing circuitry 170 executes the second ultrasound scanning (B-mode scanning) on a divided area "B" in a size twice as large as the divided area "B" illustrated in FIG. 2. In this case, the processing circuitry 170 executes the second ultrasound scanning at an updated rate twice as high as that in the case illustrated in FIG. 2.

For example, when the second ultrasound scanning on each divided area "B" is performed as illustrated in (1) and (3) in FIG. 5, tissue image data (image) corresponding to the whole second scanning area is generated. Each time the second ultrasound scanning on each divided area "B" is performed as illustrated in (5), (7) . . . in FIG. 5, a half of the tissue data is updated. In this manner, the processing circuitry 170 updates the whole tissue image data with respect to the second scanning area by performing the second ultrasound scanning twice, thereby increasing the update rate. When the update rate increases, for example, updating each divided area from the left to the right becomes inconspicuous and this fixes the wavy look. In this manner, the ultrasound diagnostic apparatus 1 is able to improve the quality of the displayed image according to the change of the range of the flow-velocity value.

The first embodiment has been described as the case where the time of the difference between the transmitting/receiving time after the change and the transmitting/receiving time before the change is assigned to the time for extending the length of the divided area in the orientation direction; however, embodiments are not limited to this. Modifications 1 to 3 of the first embodiment will be described below.

Modification 1 of First Embodiment

A case where the time of the difference is assigned to a time for increasing the density of scanning lines in the second scanning area will be described as Modification 1 of the first embodiment.

Figure 6:
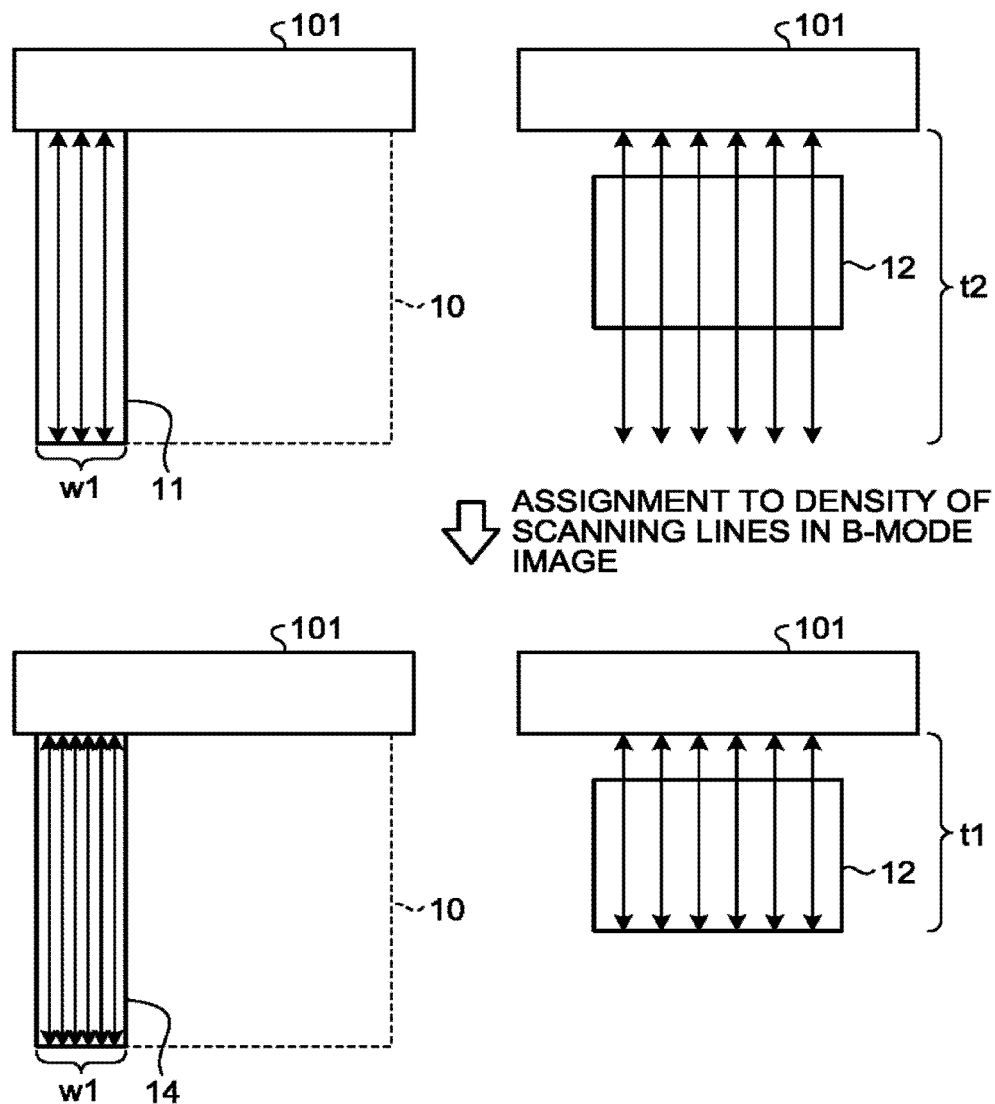
FIG. 6 is a diagram for explaining processing of an assigning function according to Modification 1 of the first embodiment.

FIG. 6 is a diagram for explaining processing performed by the assigning function 172 according to Modification 1 of the first embodiment. FIG. 6 exemplifies that the scanning conditions of the first ultrasound scanning (Doppler-mode scanning) and the second ultrasound scanning (B-mode scanning) are changed according to a change of the flow-velocity range. The drawings on the left among the upper and lower diagrams in FIG. 6 illustrate the whole second scanning area 10 and the divided area 11 in the second ultrasound scanning that is executed by the ultrasound probe 101. The drawings on the right illustrate the first scanning area 12 in the first ultrasound scanning that is executed by the ultrasound probe 101. With respect to FIG. 6, the processing of calculating a transmitting/receiving time "t2" after the change, which is the processing performed by the assigning function 172, is the same as that illustrated in FIG. 3 and therefore descriptions thereof will be omitted.

As illustrated in the upper drawings in FIG. 6, the assigning function 172 calculates the transmitting/receiving time "t2" per scanning line required to display the range of the flow-velocity value that is changed with the PRF lowering according to the instruction. The calculated transmitting/receiving time "t2" after the change is longer than the transmitting/receiving time "t1" before the change and therefore a latency time occurs as in the case illustrated in FIG. 3.

Then, as illustrated in the lower drawings in FIG. 6, the assigning function 172 then assigns the latency time to a time for increasing the density of scanning lines of a B-mode image. Accordingly, the processing circuitry 170 executes the second ultrasound scanning on a divided area 14 having the increased density of scanning lines.

Specifically, first of all, the assigning function 172 calculates the number of scanning lines NumAddRaster on which the transmitting/receiving can be performed during the latency time ΔT[s] in the second ultrasound scanning, by using the above-described Equations (1) and (2). Accordingly, for example, the processing circuitry 170 adds the number of scanning lines that is calculated by the assigning function 172 to the divided area 11, thereby obtaining the divided area 14. In the example illustrated in the lower drawings in FIG. 6, the processing circuitry 170 adds the calculated number of scanning lines without changing the length "w1" of the divided area 11 in the orientation direction, thereby obtaining the divided area 14 having the increased density of scanning lines.

As a result, after the flow-velocity range is changed, the processing circuitry 170 performs the second ultrasound scanning on the divided area 14 having the increased density of scanning lines and performs the first ultrasound scanning in the transmitting/receiving time "t1" per scanning line. Accordingly, the density of scanning lines in each divided area increases, which allows the processing circuitry 170 to increase the azimuth resolution of the B-mode scanning.

Modification 2 of First Embodiment

A case where the time of the difference is assigned to a time for increasing the density of scanning lines in the first scanning area will be described as Modification 2 of the first embodiment.

Figure 7:
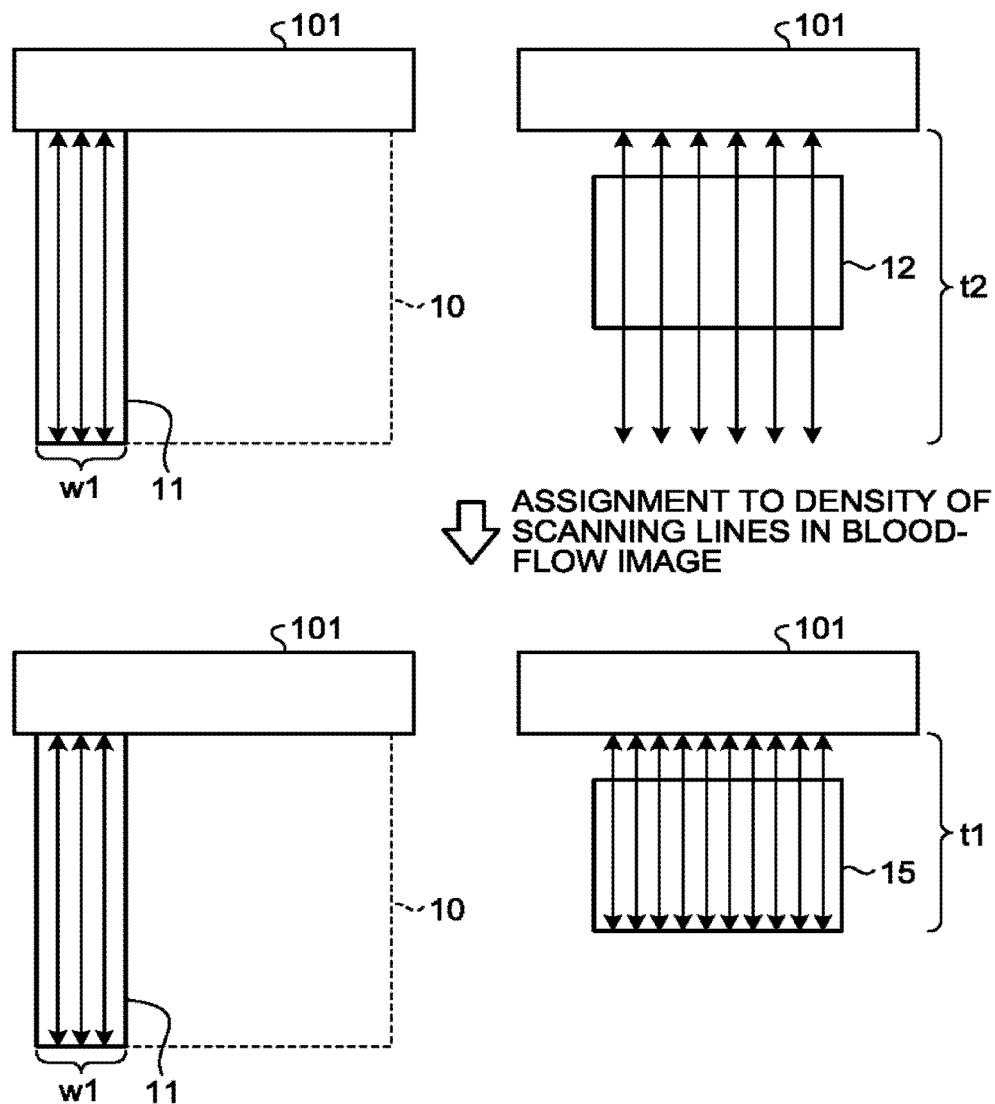
FIG. 7 is a diagram for explaining processing of an assigning function according to Modification 2 of the first embodiment.

FIG. 7 is a diagram for explaining processing performed by the assigning function 172 according to Modification 2 of the first embodiment. FIG. 7 exemplifies that the scanning conditions of the first ultrasound scanning (Doppler-mode scanning) and the second ultrasound scanning (B-mode scanning) are changed according to a change of the flow-velocity range. The drawings on the left among the upper and lower diagrams in FIG. 7 illustrate the whole second scanning area 10 and the divided area 11 in the second ultrasound scanning that is executed by the ultrasound probe 101. The drawings on the right illustrate the first scanning area 12 in the first ultrasound scanning that is executed by the ultrasound probe 101. With respect to FIG. 7, the processing of calculating a transmitting/receiving time "t2" after the change, which is the processing performed by the assigning function 172, is the same as that illustrated in FIG. 3 and therefore descriptions thereof will be omitted.

As illustrated in the upper drawings in FIG. 6, the assigning function 172 calculates the transmitting/receiving time "t2" per scanning line required to display the range of the flow-velocity value that is changed with the PRF lowering according to the instruction. The calculated transmitting/receiving time "t2" after the change is longer than the transmitting/receiving time "t1" before the change and therefore a latency time occurs as in the case illustrated in FIG. 3.

Then, as illustrated in the lower drawings in FIG. 7, the assigning function 172 then assigns the latency time to a time for increasing the density of scanning lines of a blood-flow image. Accordingly, the processing circuitry 170 executes the first ultrasound scanning on a first scanning area 15 having the increased density of scanning lines.

Specifically, first of all, the assigning function 172 calculates the latency time ΔT[s] by using the above-described Equation (1). The assigning function 172 then calculates the number of scanning lines NumAddRaster on which the transmitting/receiving can be performed during the latency time ΔT[s] in the first ultrasound scanning by using the following Equation (3). Note that the solution of Equation (3) is rounded to the closest whole number.

$$\text{NumAddRaster} = \Delta T / t1 \quad (3)$$

In this manner, from the latency time ΔT, the assigning function 172 calculates the number of scanning lines NumAddRaster that can be added in the first ultrasound scanning. For example, the processing circuitry 170 adds the number of scanning lines that is calculated by the assigning function 172 to the first scanning area 12 to obtain the scanning area 15. In the example illustrated in the lower diagrams in FIG. 7, the processing circuitry 170 adds the calculated number of scanning lines to the area having the same size as that of the first scanning area 12 to obtain the scanning area 15 having the increased number of scanning lines.

As a result, after the flow-velocity range is changed, the processing circuitry 170 performs the second ultrasound scanning on the same divided area 11 as that before the change and performs the first ultrasound scanning on the scanning area 15 having the increased density of scanning lines. Accordingly, the processing circuitry 170 increases the density of scanning lines in the Doppler-mode scanning area, which makes it possible to increase the azimuth resolution of the Doppler-mode scanning.

Modification 3 of First Embodiment

A case where the time of the difference is assigned to at least two of a time for increasing the length of the divided area in the orientation direction, a time for increasing the density of scanning lines in the first scanning area, and a time for increasing the density of scanning lines in the second scanning area will be described as Modification 3 of the first embodiment.

FIG. 8 is a diagram for explaining processing performed by the assigning function 172 according to Modification 3 of the first embodiment. FIG. 8 exemplifies that the scanning conditions of the first ultrasound scanning (Doppler-mode scanning) and the second ultrasound scanning (B-mode scanning) are changed according to a change of the flow-velocity range. The drawings on the left among the upper and lower diagrams in FIG. 8 illustrate the whole second scanning area 10 and the divided area 11 in the second ultrasound scanning that is executed by the ultrasound probe 101. The drawings on the right illustrate the first scanning area 12 in the first ultrasound scanning that is executed by the ultrasound probe 101. With respect to FIG. 8, the processing of calculating a transmitting/receiving time "t2" after the change, which is the processing performed by the assigning function 172, is the same as that illustrated in FIG. 3 and therefore descriptions thereof will be omitted.

As illustrated in the upper drawings in FIG. 8, the assigning function 172 calculates the transmitting/receiving time "t2" per scanning line required to display the range of the flow-velocity value that is changed with the PRF lowering according to the instruction. The calculated transmitting/receiving time "t2" after the change is longer than the transmitting/receiving time "t1" before the change and therefore a latency time occurs as in the case illustrated in FIG. 3.

Then, as illustrated in the lower drawings in FIG. 8, the assigning function 172 then assigns the latency time to, for example, a time for increasing the length "w1" of the divided area in the orientation direction and a time for increasing the density of scanning lines of a blood-flow image. For example, the processing circuitry 170 performs the second ultrasound scanning by using a divided area 16 obtained by increasing the length to "w3" by adding scanning lines and performs the first ultrasound scanning on a scanning area 17 having the increased density of scanning lines. Accordingly, the processing circuitry 170 is able to increase the update rate of the B-mode scanning and the azimuth resolution of the Doppler-mode scanning.

FIG. 8 illustrates the case where the latency time is assigned to the time for increasing the length of the divided area in the orientation direction and the time for increasing the density of scanning lines in the blood-flow image; however, embodiments are not limited to this. For example, the assigning function 172 may assign the latency time to at least one of the time for increasing the length of the divided area in the orientation direction, the time for increasing the density of scanning lines in the first scanning area, and the time for increasing the density of scanning lines in the second scanning area.

Another Embodiment

In addition to the above-described embodiments, various different embodiments may be performed.

Specifying Quotas

For example, Modification 3 of the first embodiment is described as the case where the latency time is assigned to the time to increase at least one of the update rate of the B-mode scanning, the azimuth resolution of the B-mode scanning, and the azimuth resolution of the Doppler-mode scanning, and it is possible for the operator to adjust the ratio of the assigning (quotas) as appropriate while looking at the displayed image.

FIG. 9 is a diagram for explaining the processing performed by the ultrasound diagnostic apparatus 1 according to another embodiment. FIG. 9 exemplifies a case where the operator adjusts the quotas while looking at a blood-flow image 21 that is displayed on a tissue image 20.

As illustrated in the upper drawing in FIG. 9, when the operator issues an instruction for lowing the upper limit value "1.0 cm/s" of a scale 22 of the flow-velocity range, the upper limit value of the scale 22 is lowered to "0.7 cm/s" by lowering the PRF of the first ultrasound scanning. With the PRF lowering, the assigning function 172 calculates "t2" longer than "t1" as the time for transmitting/receiving ultrasound per scanning line required to display the range of the flow-velocity range that is changed according to the instruction. The assigning function 172 then performs the processing described with reference to FIG. 3 to assign the time of the difference between "t2" and "t1" to the time for increasing the update rate of the B-mode scanning.

When the flow-velocity range is changed, as illustrated in the intermediate diagram in FIG. 9, the receiving function 171 displays quota display areas 23, 24 and 25 as a GUI enabling adjustment of the quotas on the display 103. The quota display area 23 is an area in which the quota assigned to the time to increase the update rate of the B-mode scanning (B update rate) is displayed. The quota display area 23 contains a scale representing the level of quota and a pointer 26 above the scale. The quota display area 24 is an area in which the quota assigned to the time to increase the azimuth resolution of the B-mode scanning (B resolution) is displayed. The quota display area 24 contains a scale representing the level of quota and a pointer 27 above the scale. The assignment ratio display area 25 is an area in which the quota assigned to the time to increase the azimuth resolution of the Doppler-mode scanning (D resolution) is displayed. The quota display area 25 contains a scale representing the level of quota and a pointer 28 above the scale. The pointers 26, 27, and 28 illustrated in FIG. 9 represent that, the more the pointer is positioned rightward, the higher the quota is and that, the more the pointer is positioned leftward, the lower the quota is. According to the intermediate diagram in FIG. 9, all the time of the difference is assigned to the update rate of the B-mode scanning and therefore the pointer 26 is positioned at the right end of the scale and the pointers 27 and 28 are positioned at the left ends of the scales.

When the operator performs an operation of moving the position of each of the pointers 26, 27 and 28, the receiving function 171 receives the operation as an instruction for changing the quotas. For example, as illustrated in the lower diagram in FIG. 9, while looking at the tissue image 20 and the blood-flow image 21, the operator moves the pointer 26 leftward by three markings, moves the pointer 27 rightward by one marking, and moves the pointer 28 rightward by two markings. The receiving function 171 receives this operation as an instruction for changing the quotas represented in the intermediate diagram in FIG. 9 to the quotas illustrated in the lower diagram in FIG. 9.

The assigning function 172 then assigns the time of the difference according to the quotas that are received by the receiving function 171. In the example illustrated in the lower diagram in FIG. 9, the assigning function 172 lowers the quota to the update rate of the B-mode scanning by three markings, increases the quota to the azimuth resolution of the B-mode scanning by one marking, and increases the quota to the azimuth resolution of the Doppler-mode scanning by two marking. The assigning function 172 assigns, according to the changed quotas, the time of the difference to each of the times for the update rate of the B-mode scanning, the azimuth resolution of the B-mode scanning, and the azimuth resolution of the Doppler-mode scanning.

As described above, when the time of the difference is assigned to at least two of the time for increasing the length of the divided area in the orientation direction, the time for increasing the density of scanning lines in the first scanning area, and the time for increasing the density of scanning lines in the second scanning area, the receiving function 171 further receives an instruction for changing the quotas assigned to the respective times. The assigning function 172 then assigns the time of the difference according to the quotas. The operator is thus able to adjust the quotas as appropriate while looking at the displayed image, such as the tissue image 20 and the blood-flow image 21.

FIG. 9 only illustrates an example. For example, the quotas may set in advance. In this case, for example, on the basis of the pre-set quotas, the assigning function 172 assigns the time of the difference to each of the times for the update rate of the B-mode scanning, the azimuth resolution of the B-mode scanning, and the azimuth resolution of the Doppler-mode scanning.

Switching Between Assignment Destination

Switching between the update rate of the B-mode scanning, the azimuth resolution of the B-mode scanning, and the azimuth resolution of the Doppler-mode scanning to which the time of the difference is assigned may be switched according to an external trigger.

For example, the assigning function 172 is able to switch the destination to which the time of the difference to occur between the update rate of the B-mode scanning, the azimuth resolution of the B-mode scanning, and the azimuth resolution of the Doppler-mode scanning in the order they appear in this sentence. Furthermore, when the ultrasound diagnostic apparatus 1 is able to detect an ECG signal, the assigning function 172 is able to switch the destination to which the time of the difference is assigned according to given ECG signals (of, for example, the diastole and systole). Furthermore, for example, the assigning function 172 is able to monitor the correlation value of a tomographic image in the time direction (B-mode image) and, when the correlation value represents a given change, switch the destination to which the time of the difference is assigned.

The components of each device illustrated in the drawings are of functional ideas and are not necessarily required to be configured physically as illustrated in the drawings. In other words, embodiments of distribution and integration of each device are not limited to those illustrated in the drawings, and all or part of the embodiments may be dispersed or integrated functionally or physically according to any unit and according to various types of loads and the environment of use. Furthermore, all or part of each processing function performed by each device may be implemented by a CPU and a program that is analyzed and executed by the CPU, or may be implemented as hardware using a wired logic.

All or part of each set of processing described as processing that is automatically performed with respect to the above-described embodiments may be performed manually, or all or part of each set of processing described as processing that is manually performed may be performed automatically. Furthermore, information including the processing procedures, control procedures, specific names, and information including various types of data and parameters described and illustrated in the document and drawings may be freely changed unless otherwise noted.

Furthermore, the ultrasound imaging method described with respect to the above-described embodiments may be implemented by a computer, such as a personal computer or a work station, by executing an ultrasound imaging program prepared in advance. The ultrasound imaging method may be distributed via a network, such as the Internet. The ultrasound imaging method may be recorded in a computer-readable recording medium, such as a hard disk, a flexible disk (FD), a CD-ROM, a MO or a DVD, may be read from the recording medium by a computer, and thus may be executed.

According to at least one of the embodiments described above, it is possible to improve the image quality of a displayed image according to a change of the range of the flow velocity value.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus comprising:
processing circuitry configured to:
control an ultrasound probe to execute first ultrasound scanning to acquire blood flow information within a first scanning area and to scan in a first transmitting and receiving time per scanning line of the first ultrasound scanning;
control the ultrasound probe to execute second ultrasound scanning to acquire tissue shape information within a second scanning area;
control a display to display the blood flow information based on a pre-set range of a flow-velocity value;
receive an instruction for changing the range of the flow-velocity value;
calculate a second transmitting and receiving time per scanning line corresponding to the range of the flow-velocity value changed in accordance with the instruction;
determine whether the second transmitting and receiving time is larger than the first transmitting and receiving time;
when the second transmitting and receiving time exceeds the first transmitting and receiving time, assign a time of an excess of the second transmitting and receiving time relative to the first transmitting and receiving time to at least one of the first ultrasound scanning and the second ultrasound scanning as part of time-sharing between the first and second ultrasound scanning; and
display changes in the range of the flow-velocity value and an indication of the assignment of the time of the excess.

2. The ultrasound diagnostic apparatus according to claim 1, wherein the processing circuitry is configured to control the ultrasound probe to execute, as the second ultrasound scanning, ultrasound scanning on each of multiple divided areas obtained by dividing the second scanning area during the first ultrasound scanning through the time sharing.

3. The ultrasound diagnostic apparatus according to claim 2, wherein the processing circuitry is configured to
receive an instruction for lowering an upper limit value of a range of the flow-velocity value, and
upon receiving the instruction for lowering the upper limit value of the range of the flow-velocity value, assign the time of the excess to at least one of a time for increasing a length of the respective divided areas in an orientation direction, a time for increasing a density of scanning lines in the first scanning area, and a time for increasing a density of scanning lines in the second scanning area.

4. The ultrasound diagnostic apparatus according to claim 3, wherein the processing circuitry is configured to
when the time of the excess is assigned to at least two of the time for increasing the length of the respective divided areas in an orientation direction, the time for increasing the density of scanning lines in the first scanning area, and the time for increasing the density of scanning lines in the second scanning area, further receive an instruction for changing quotas assigned to the respective times, and
assign the time of the excess to at least two of the times according to the quotas.

5. The ultrasound diagnostic apparatus according to claim 3, wherein the processing circuitry is configured to, when the time of the excess is assigned to at least two of the time for increasing the length of the divided area in an orientation direction, the time for increasing the density of scanning lines in the first scanning area, and the time for increasing the density of scanning lines in the second scanning area, assign the time of the excess to at least two of the times on the basis of a ratio of the assigning that is previously set.

* * * * *